US006778916B2

(12) United States Patent
Lee

(10) Patent No.: US 6,778,916 B2
(45) Date of Patent: Aug. 17, 2004

(54) BALL INDENTER UTILIZING FEA SOLUTIONS FOR PROPERTY EVALUATION

(76) Inventor: Hyung Yil Lee, 2003 Dae Hwa Dong, Illsan Gu, Kunyung Villa 1502-304, Koyang City Kyunggi Do (KR), 411-410

( * ) Notice: Subject to any disclaimer, the term of this patent is extended or adjusted under 35 U.S.C. 154(b) by 0 days.

(21) Appl. No.: 10/193,909

(22) Filed: Jul. 15, 2002

(65) Prior Publication Data

US 2003/0080721 A1 May 1, 2003

(30) Foreign Application Priority Data

Jul. 23, 2001 (KR) .......................................... 2001-44221

(51) Int. Cl.[7] .............................. G06F 19/00; G01L 1/00; G01N 3/48
(52) U.S. Cl. .............................. 702/42; 702/35; 702/43; 73/81
(58) Field of Search .............................. 702/33, 34, 35, 702/42, 43, 91, 104, 166–168; 73/81, 82, 789, 573, 575

(56) References Cited

U.S. PATENT DOCUMENTS

| | | | | |
|---|---|---|---|---|
| 4,852,397 A | * | 8/1989 | Haggag | 73/82 |
| 6,134,954 A | * | 10/2000 | Suresh et al. | 73/81 |
| 6,289,734 B1 | * | 9/2001 | Daugela | 73/573 |
| 6,311,135 B1 | * | 10/2001 | Suresh et al. | 702/43 |

* cited by examiner

Primary Examiner—Bryan Bui
(74) Attorney, Agent, or Firm—G W i P S

(57) ABSTRACT

An automated indentation system based on finite element solutions or performing a non-destructive compression test by loading a compressive indentation load (P) and calculating a elastic modulus (E) and a yield strength ($\sigma_0$), and a hardening exponent (n) from measured indentation depth ($h_r$) and indentation load (P), and unloading slope (S). The system comprises a stepmotor control system (1), a measurement instrumentation (2) having a load cell (15), laser displacement sensor (17) for measuring the indentation depth and ball indenter (18), a data acquisition system (3) having an signal amplifier for amplifying and filtering signals from the load cell (15) and laser displacement sensor (17), and a control box (4) pre-stored computer programming algorisms for adjusting and controlling the moving speed and direction of stepmotor (12). The control box (4) enables storing and retrieving the signals of measured data and material properties, and plotting the graphs of load-depth curve and stress-strain curves based on the signal data. The procedure of computer programming algorithm is as follows: First, the Young's modulus E is computed from Eq. (29) by using slope S and initially guessed values of n and $\epsilon_0$. Then, $c^2$, $\epsilon_p$ and $\sigma$ are calculated as many as the number of load and depth data. From these, the values of n, K, $\sigma_0$ and $\epsilon_0$ are calculated from stress-strain relation. And then updated E, d, $c^2$, $\epsilon_p$, $\sigma$, n, K, $\sigma_0$ and $\epsilon_0$ are repeatedly calculated until the updated $\epsilon_0$ and n are converged within the tolerance.

16 Claims, 14 Drawing Sheets

(a) FE load-depth curves (b) Unloading slopes (a) Variation of $k_1$ with hardening exponent $n$  (b) Extrapolation of $k_1$ to $n=1$ (a) $E$ vs $S/d$ curve  (b) Second coefficient of Young's modulus equation

BALL INDENTER UTILIZING FEA SOLUTIONS FOR PROPERTY EVALUATION

BACKGROUND OF THE INVENTION

1. Field of the Invention

The present invention relates to a ball indentation tester and testing technique being used to measure the material properties when tensile test cannot be applied; welding parts with continuous property variation, brittle materials with unstable crack growth during preparation and test of specimen, and the parts in present structural use. More particularly, indentation test is non-destructive and easily applicable to obtain material properties. A new numerical indentation technique is invented by examining the finite element solutions based on the incremental plasticity theory with large geometry change. The load-depth curve from indentation test successfully converts to a stress-strain curve.

2. Background of the Related Art

While indentation test is non-destructive and easily applicable to obtain material properties, the test result is difficult to analyze because of complicated triaxial stress state under ball indenter. For this reason, the indentation test is inappropriate to measure various material properties. Thus, it is used to obtain merely hardness. Recently, however, this kind of difficulty is greatly overcome both by finite element analyses of subindenter stress and deformation fields, and by continuous measurement of load and depth. As a result, stress-strain relation can be obtained from analysis of load-depth curve.

An automated indentation test gives a stress-strain curve from measured load-depth data. FIG. 1 shows a schematic profile of indentation. Here $h_t$ and $d_t$ are ideal indentation depth and projected diameter at loaded state, and $h_p$ and $d_p$ are plastic indentation depth and projected diameter at unloaded state. With an indenter of diameter D, the following relation is delivered from spherical geometric configuration.

$$d_t = 2\sqrt{h_t D - h_t^2} \tag{1}$$

Assuming that "projected" indentation diameter at loaded and unloaded states remains the same as shown in FIG. 2, Hertz expressed d ($=d_t=d_p$ under this assumption) as follows.

$$d = 2.22\left\{\frac{P}{2}\frac{r_1 r_2}{r_2 - r_1}\left(\frac{1}{E_1} - \frac{1}{E_2}\right)\right\}^{1/3} \tag{2}$$

where $r_1$ and $r_2$ are indentation radius of indenter and specimen at unloaded state, and $E_1$ and $E_2$ are Young's modulus of indenter and specimen, respectively. If the indenter is rigid, $r_1 = D/2$ and $r_2$ is a function of d and $h_p$.

Substituting these into Eq. (3) gives:

$$d = \left[\frac{0.5CD\{h_p^2 + (d/2)^2\}}{h_p^2 + (d/2)^2 - h_p D}\right]^{1/3} \tag{3}$$

where C is 5.47P $(E_1^{-1} + E_2^{-1})$.

Tabor brought the experimental conclusion that equivalent (plastic) strain "at the (Brinell and Micro Vickers) indenter contact edge" is given by:

$$\varepsilon_p = 0.2\left(\frac{d}{D}\right) \tag{4}$$

where d is calculated from Eq. (2). But, Haggag et al. ignored pile-up and sink-in of material. They simply calculated the indentation diameter d with Eq. (1) at loaded state and plastic diameter $d_p$ with Eq. (3) at unloaded state, and plastic strain with Eq. (4) by substituting $d_p$ for d.

Mean contact pressure $p_m$ is defined by $p_m = 4P/(\pi d^2)$, where P is the compressive indentation load. Then constraint factor $\psi$, which is a function of equivalent plastic strain, is defined as the ratio between mean contact pressure and equivalent stress.

$$\psi(\varepsilon_p) = p_m/\sigma \tag{5}$$

Hence, the equivalent stress is expressed in the form:

$$\sigma = \frac{4P}{\pi d^2 \psi} \tag{6}$$

Note that, in a strict sense, both equivalent plastic strain and equivalent stress are functions of location within the subindenter deformed region as well as deformation intensity itself. Thus constraint factor $\psi$ is also a function of location. Francis classified the indentation states into three regions and presented the empirical formula for $\psi$ with indentation test results for the various materials taken into consideration.

(1) Elastic region with recoverable deformation
(2) Transient region with elastic-plastic deformation
(3) Fully plastic region with dominant plastic deformation Haggag et al. calculated stress-using $d_p$ instead of d in Eq. (6), and they modified Francis' constraint factor considering that constraint factor is a function of strain rate and strain hardening.

$$\psi = \begin{cases} 1.12 & \phi \leq 1 \\ 1.12 + \tau \ln\phi & 1 \leq \phi \leq 27 \\ \psi_{max} & \phi \geq 27 \end{cases} \tag{7a}$$

$$\psi_{max} = 2.87\alpha_m \tag{7b}$$

$$\tau = (\psi_{max} - 1.12)/\ln 27 \tag{7c}$$

where $\alpha_m$ is constraint factor index. It is proportional to strain rate, and has the value of 1 for the material with low strain rate. By investigating the experimental results, Francis suggested a normalized variable $\phi$ in the form:

$$\phi = \frac{\varepsilon_p E_2}{0.43\sigma} \tag{8}$$

Since equivalent strain in Eq. (4) is the value at the indenter contact edge, all the values in Eqs. (5)–(8) implicitly mean values also at the indenter contact edge.

For spherical indenter, the following relation called Meyer's law holds between applied load P and indentation projected diameter d.

$$P = kd^m \tag{9}$$

where k and m are material constants when indenter diameter D is fixed, and m is Meyer's index generally in the range of 2 to 2.5.

Meyer's experiment reveled that index m is independent of diameter D, and k decreases with increasing D.

$$A = k_1 D_1^{m-2} = k_2 D_2^{m-2} = k_3 D_3^{m-2} = \ldots \quad (10)$$

where A is a constant. Substituting this into Eq. (9) gives:

$$\frac{P}{d^2} = A\left(\frac{d}{D}\right)^{m-2} \quad (11)$$

Equation (6) converts to Eq. (12) by Eq. (11).

$$\sigma = \frac{4A}{\pi \psi}\left(\frac{d}{D}\right)^{m-2} \quad (12)$$

After replacing d with $d_t$ in Eq. (11), Haggag et al. calculated yield strength $\sigma_0$ from the following relation of yield strength and slope A that George et al. obtained from experiment.

$$\sigma_0 = \beta_m A \quad (13)$$

where $\beta_m$ is a material constant. The value of $\beta_m$ in steel is about 0.229, which comes from analysis of tensile yield strength and A.

Rice and Rosengren proposed a stress-strain relation in piecewise power law form.

$$\frac{\varepsilon_t}{\varepsilon_o} = \begin{cases} \frac{\sigma}{\sigma_o} & \text{for } \sigma \leq \sigma_o \\ \left(\frac{\sigma}{\sigma_o}\right)^n & \text{for } \sigma > \sigma_o; 1 < n \leq \infty \end{cases} \quad (14)$$

where $\sigma_0$ is yield strength, $\epsilon_0 = \sigma_0/E$ yield strain and n strain hardening exponent. Total strain $\epsilon_t$ is decomposed into elastic and plastic strains ($\epsilon_t = \epsilon_e + \epsilon_p$).

FIG. 3 shows the calculation process of the material properties by Haggag's indentation method. In the approach of Haggag et al., each repetition of loading and unloading provides one point of stress-strain data points. Thus a single indentation test usually picks up total only 6–7 data point. The approach also requires prior material constants from extra tensile tests.

The Haggag's model for the SSM system adopts the indentation theories of Francis and Tabor established on the experimental observations and some analyses. Haggag's approach requires prior material constants from extra tensile tests, which is one of the shortcomings.

The SSM system gives stress-strain curves through regression of load-depth data obtained from 6–7 times repetitive loading and unloading. This insufficient number of data often leads to inaccurate regression. Above all, the most critical issue in Haggag's approach is that subindenter stress field from deformation theory is far from the real one.

SUMMARY OF THE INVENTION

In order to overcome the disadvantages as described above, the present invention provides an automated indentation system for performing a compression test by loading a compressive indentation load (P). Then, an elastic modulus (E), a yield strength ($\sigma_0$), and a hardening exponent (n) are calculated based on measured indentation depth ($h_t$) and indentation load (P), and unloading slope (S).

The automated indentation system of the present invention comprises a stepmotor control system (1), measurement instrumentation (2) data acquisition system (3) and control box (4).

The stepmotor (12) is adopted for precisely controlling a traveling distance and minimizing vibration of motor.

The measurement instrumentation (2) consists of a load cell (15), a laser displacement sensor (17) for measuring the indentation depth, and a ball indenter (18).

The data acquisition system (3) includes a signal amplifier for amplifying and filtering signals received from the load cell (15) and laser displacement sensor (17).

The control box (4) is pre-stored computer programming algorisms for adjusting and controlling moving speed and direction of the stepmotor (12). It also enables to perform calculations and plot the graphs of load-depth curve or strain-stress curves according to the amplified signal data, and store and retrieve the measured signal data, material properties and produced data.

The stepmotor control system (1) comprises a cylindrical linear actuator having a ball screw (14) and backlash nut (16) for suppressing backlash, a flexible coupling (13) being connected to the ball screw (14) and stepmotor (12) for constraining the rotation and high repeatability. The stepmotor control system (1) also enables to control acceleration/deceleration of the stepmotor (12) and regulating velocity with repeatability of 3~5%.

The load cell (15) is specified based on the performance of finite element simulation of indentation test. The indentation load (P) is dependent on the ball size and material properties, and maximum indentation load is under 100 kgf for 1 mm indenter.

The laser displacement sensor for measuring indentation depth is connected parallel to a linear actuator, and measurement range of laser displacement sensor (17) is 4 mm and resolution is 0.5 $\mu$m.

The ball indenter (18) is an integrated spherical indenter being made of tungsten carbide (WC) for precisely measuring an indented depth, and a diameter of indenter tip is 1 mm.

Generally, the measured indentation depth ($h_{exp}$) contains an additional displacement due to system compliance ($h_{add}$). Therefore, in order to obtain an accurate indentation depth, the practical indentation depth is compensated by a displacement relationship between the measured indentation depth ($h_{exp}$) and an actual indentation depth ($h_{FEM}$) obtained from FEA.

A computer programming algorism is provided for performing an automated indentation test by loading a compressive indentation load (P), calculating an elastic modulus (E) and a yield strength ($\sigma_0$), and a hardening exponent (n) from measured indentation depth ($h_t$) and indentation load (P), and unloading slope (S), then plotting a stress-strain curve of the indented material.

The process of computer programming algorism comprises the steps of: inputting data of measured indentation depth ($h_t$), load (P) and unloading slope (S) from pre-stored data, computing a Young's modulus (E) from unload slope and initially guessed values of n and $\epsilon_0$, computing indentation diameters (d) from $c^2$ equation as many as the number of load and depth data, computing equivalent plastic strains ($\epsilon_p$) and equivalent stresses ($\sigma$) according to the calculated indentation diameters (d), computing values of strain hardening exponent (n) and K from stress-strain relation, computing a yield stress ($\sigma_0$) and strain ($\epsilon_0$), computing updated E, d, $c^2$, $\epsilon_p$, $\sigma$, n, K, $\sigma_0$, and $\epsilon_0$ until the updated $\epsilon_0$ and n are converged within the tolerance, and outputting material properties (E, $\sigma_0$, n) and plotting the stress-strain curve.

DETAILED DESCRIPTION OF THE PREFERRED EMBODIMENT

The objectives and advantages of the present invention will be more clearly understood through the following detailed descriptions accompanying with the drawings.

Figure 1:
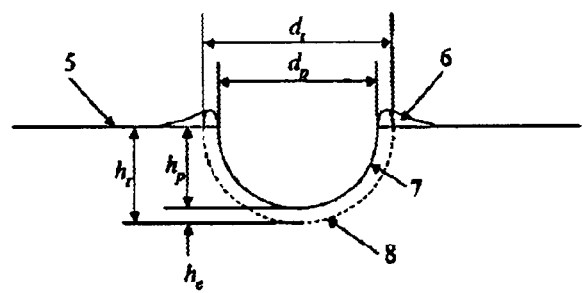
FIG. 1 illustrates a schematic profile of typical indentation.
Figure 2:
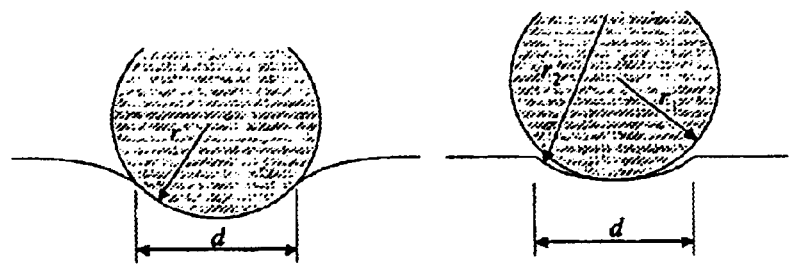
FIG. 2 is a projected indentation diameter at loaded and unloaded states.
Figure 4:
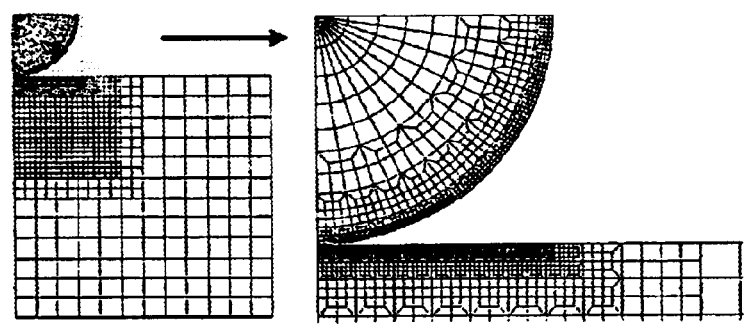
FIG. 4 is a finite element (FE) model for a ball indentation test.
Figure 3:
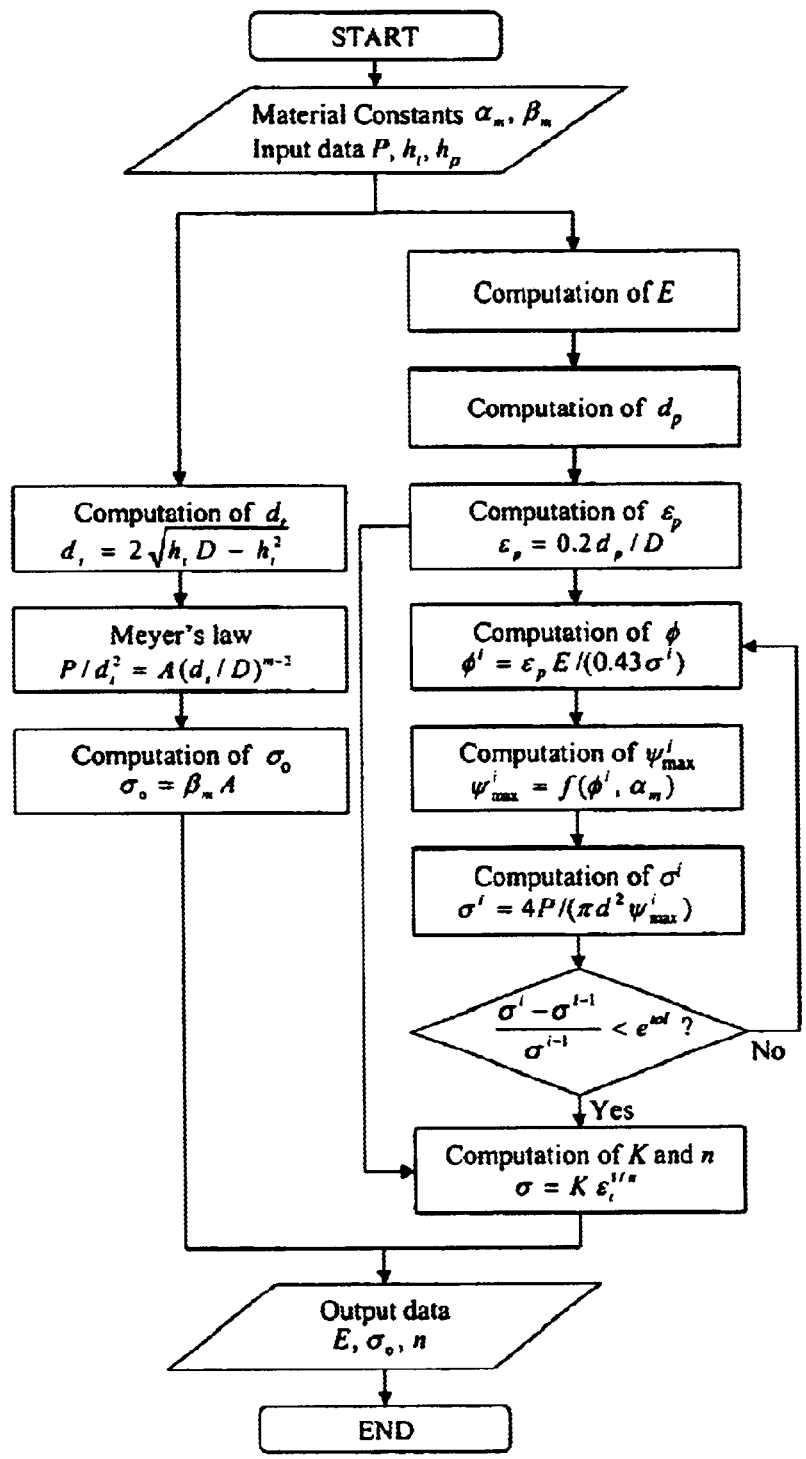
FIG. 3 is a calculation process of the material properties.

As shown in FIG. 4, a finite element (FE) model is provided for a ball indentation test. The FE analysis of large deformation is performed by using isotropic elasto-plastic material, which follows the $J_2$ flow theory. Considering both loading and geometric symmetry, the four nodes of axisymmetric elements CAX4 (ABAQUS, 2002) are applied. The preliminary analyses are revealed that the eight nodes CAX8 element has a trouble of discontinuous equivalent plastic strain at its mid-node. The lower degree of CAX4 shape function is supplemented by placing fine elements with size 0.25% of indenter diameter at the material contact surface. MPC (Multi-Point Constraints) is conveniently used at the transition region where element size changes. But constrained mid-nodes of MPC tend to give discrete stress and strain values. Thus, the trapezoidal elements are adopted in the transition region near contact surface, and use MPC in the transition region far from the contact surface. The FE model of specimen and indenter consist of about 2300 and 630 elements, respectively. The contact surfaces are also placed at both material and indenter surfaces. Axisymmetric boundary conditions are imposed on the nodes on axisymmetric axis. The indenter moves down to penetrate the material with the bottom fixed. The diameter of indenter is 1 mm, Young's modulus 650 GPa.

Indentation theories of Matthews and Hill et al. are based on the deformation theory of plasticity. Although the indentation theory is easier to develop with deformation than with incremental plasticity theory, the two theories produce quite different subindenter deformations. For example, the maximum stress occurs at the bottom part of indentation center for deformation theory, while it occurs at the surface part 0.4 d away from indentation center for incremental theory. Here d is the projected contact diameter, which takes the effect of pile-up and sink-in into consideration.

Figure 5:
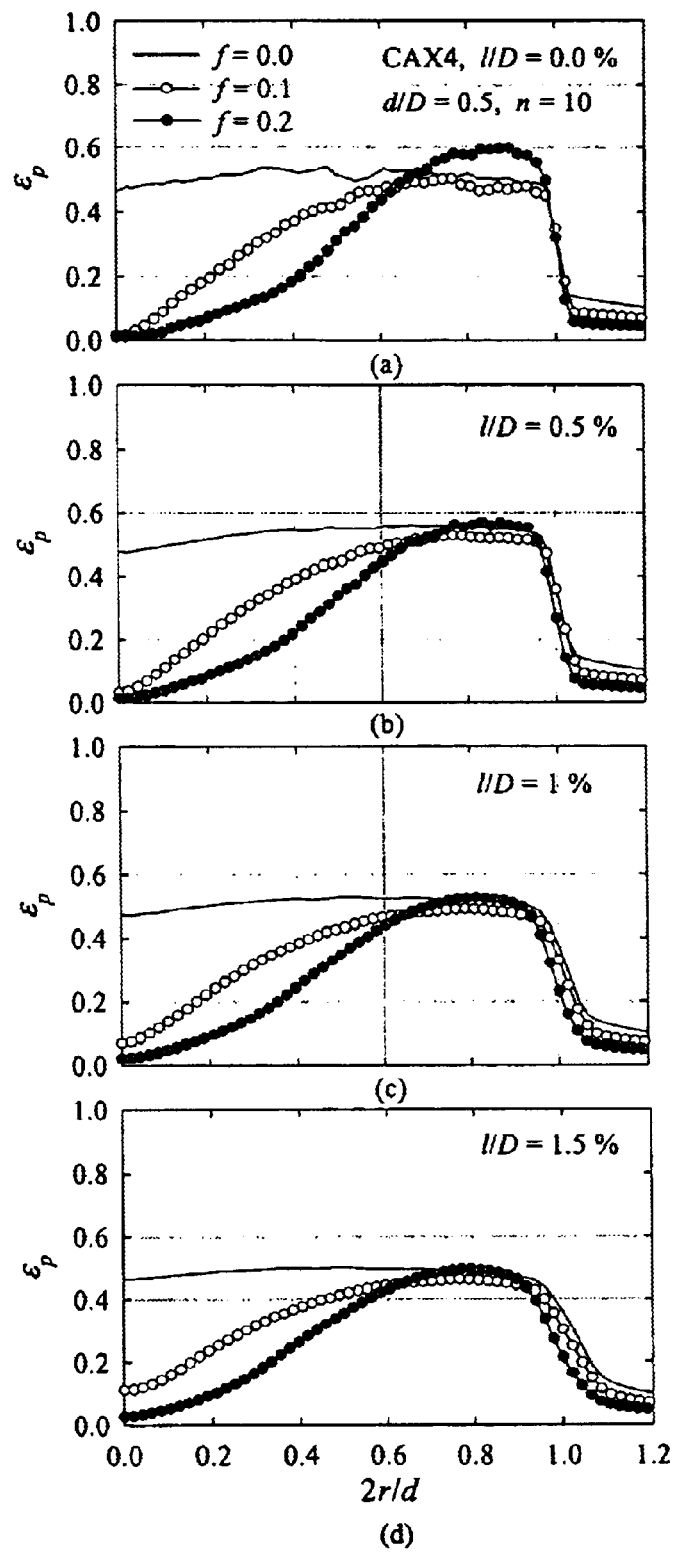
FIG. 5 is the distribution of equivalent plastic strain $\epsilon_p$ along radial direction r for strain hardening exponent n=10, friction coefficient f=0.0, 0.1 and 0.2, d/D=0.5 at specific depth l/D.

FIG. 5 shows distribution of equivalent plastic strain $\epsilon_p$ along radial direction r for strain hardening exponent n=10, friction coefficient f=0.0, 0.1 and 0.2, d/D =0.5 at specific depth l/D. Here r is the projected distance from indentation center, l is the distance from material surface to observation depth, and d/D is the ratio of projected contact diameter to indenter diameter. Equivalent plastic strain oscillates at surface due to contact problem. Oscillation and the effect of friction coefficient decreases as observing position moves downward from the surface. Thus, a new probing depth is proposed to be beneath 1% of indenter diameter from the surface (l/D=0.01). This depth is still near the surface, yet with negligible contact problem.

Distribution of equivalent strain is affected by friction coefficient as shown in FIG. 5. The value of friction coefficient between metals is commonly 0.1 to 0.2, but difficult to measure exactly. This is because it depends on the environmental factors such as temperature and humidity. Tabor suggested the acquisition point of equivalent plastic strain as r/(d/2)=1; i.e. contact edge.

However it is difficult to extract accurate stress-strain relationship from the suggested point because of sharp strain gradient and tangible effect of friction coefficient. Hence, a selection is made for the data acquisition point at 0.4 d apart from indentation center. This new point features i) negligible effect of friction coefficient, ii) quite gentle strain gradient and iii) extended strain range by a factor of five. The ground of this arbitrary selection is that the equivalent stress and strain at any point should be on uniaxial stress-strain curve, even though the equivalent stress and strain of material vary point to point, and also with indentation depth. Deformation and incremental plasticity theories provide thoroughly different stress and strain values at this new point. Consequently a new set of indentation governing equations should be developed using flow theory.

Figure 6:
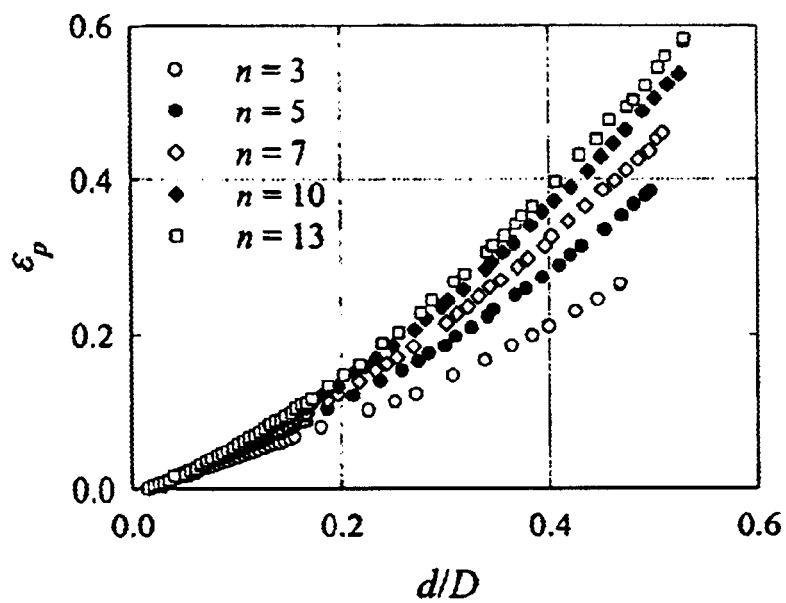
FIG. 6 illustrates a plastic strain curves at the new data acquisition point for various strain hardening exponents with the projected contact diameter.

FIG. 6 shows the plastic strain curves at the new data acquisition point for various strain hardening exponents with the projected contact diameter. Here friction coefficient f is 0.1, yield strength $\sigma_0$ 400 MPa, Young's modulus E 200 GPa. The plastic strain curve starts only slightly off the origin, which indicates that plastic deformation takes place even at shallow indentation. The plastic strain increases with strain hardening exponent, since material with larger n value deforms more easily. The data acquisition point in the prior indentation theory was the contact edge where maximum plastic strain can reach 0.2 under full indentation of hemispheric ball. But as full indentation is impractical, the maximum strain actually achieved is rather smaller than this maximum. Compared with the prior theory, the present approach provides the strain value five times greater at the same indentation depth; for example, exceeding 0.5 at d/D=0.5.

A new indentation theory is presented on the basis of FE solutions from the new optimal data acquisition point, 2r/d=0.4 and l/D=1%, where the frictional effect is ignored and obtained maximum strain for a given indentation depth. The actual projected contact diameter with pile-up and sink-in in consideration is calculated from the geometric shape of a sphere.

$$d = 2\sqrt{hD - h^2} = 2\sqrt{c^2 h_t D - (c^2 h_t)^2} \quad (15)$$

Here h is actual indentation depth due to pile-up and sink-in, $h_t$ is nominal depth measured from the reference surface (=original material surface), and $c^2$ is defined as:

$$c^2 \equiv \frac{h}{h_t} \quad (16)$$

From FIG. 6, equivalent plastic strain can be approximated in the functional form below when the values of yield strength and Young's modulus are fixed.

$$\varepsilon_{eq}^{pl} = f_o^\varepsilon(n)\left(\frac{d}{D}\right)^{f_1^\varepsilon(n)} \quad (17)$$

As mentioned above, Haggag's indentation theory necessitates prior material constants, for finding yield strength, from extra tensile tests. This complicates evaluation of material properties by using indentation test. An attempt is made to eliminate the extra process thru interrelationship of material properties. Piecewise power law relation (14) for plastic deformation becomes:

$$\sigma = \sigma_o\left(\frac{\varepsilon_t}{\varepsilon_o}\right)^{1/n} = K\varepsilon_t^{1/n} \quad (18)$$

where K is obtained by the regression of stress-strain data. As Eq. (18) is also valid for $\sigma = \sigma_0$, $$\sigma_0 = K\epsilon_0^{1/n} \quad (19)$$

Elastic stress-strain relation at the moment of yielding is Eq. (20).

$$\sigma_0 = E\epsilon_0 \quad (20)$$

Substituting (20) into Eq. (19) produces $$\sigma_o = \left(\frac{K^n}{E}\right)^{\frac{1}{n-1}} = E\left(\frac{K}{E}\right)^{\frac{n}{n-1}} \quad (21)$$

Consequently, the n and K are calculated from the regression of the stress-strain relation of Eq. (18) if the stress corresponding to strain is accurately predicted, and $\sigma_0$ is obtained from Eq. (21).

First, the FE analyses are performed for various values of strain hardening exponent with yield strain fixed to verify above formulae. It is difficult to measure the actual projected indentation diameter d. Thus, an approach is chosen for calculating d from Eq. (15) with $c^2$ obtained from regression of FE solutions.

Figure 7:
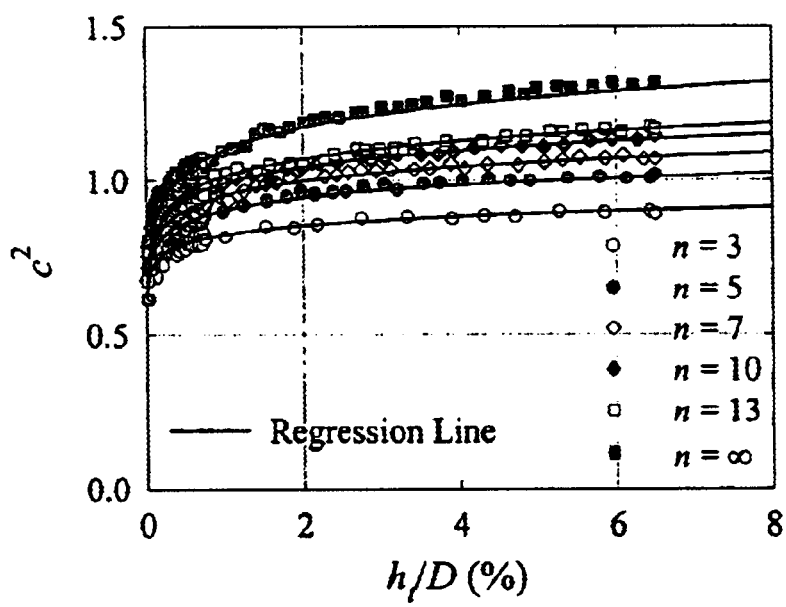
FIG. 7 is a regression curves of $c^2$ against an indentation depth for various values of n with f=0.1.

FIG. 7 illustrates regression curves of $c^2$ against indentation depth for various values of n with f=0.1. Herein, $c^2$ is calculated from the ratio of actual indentation depth to nominal indentation depth by its definition in Eq. (16). FIG. 7 reveals $c^2$ is a function of indentation depth unlike the outcome of Matthews and Hill et al. in which $c^2$ was a constant for a given value of n. At the outset of indentation, $c^2$ starts from the theoretical value 0.5 since elastic deformation is initially dominant. Then $c^2$ increases with indentation depth as plastic deformation becomes dominant. As pile-up occurs more easily with higher value of n, $c^2$ increases with n for a given indentation depth, which is consistent with the results of Matthews, Hill and Norbury and Samuel. Note that even in sufficiently indented fully plastic state, $c^2$ keeps slightly increasing, instead of saturating to a constant value, with indentation depth. Overall the prior indentation theories should be revised such that $c^2$ is a function of indentation depth as well as strain hardening exponent n. The FE solutions of $c^2$ in FIG. 7 can be expressed with the following equation.

$$c^2 = f_0^c(n) + f_1^c(n)\ln(100 h_t/D) \quad (22)$$

$$f_0^c(n) = a_{0i}^c n^{-i}; \ a_{0i}^c = (1.09, -1.21, 1.13)$$

$$f_1^c(n) = a_{1i}^c n^{-i}; \ a_{1i}^c = (0.104, -0.323, 0.405)$$

where a is a coefficient of polynomial function.

Figure 8:
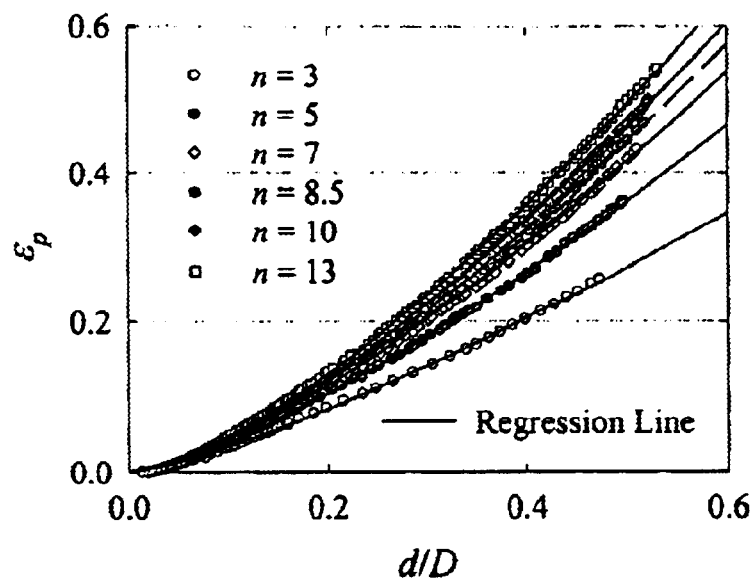
FIG. 8 is a FE solution and corresponding regression curves of equivalent plastic strain $\epsilon_p$ against the projected contact diameter for various values of n at l/D=1% and 2r/d=0.4 for f=0.1.

FIG. 8 shows the FE solutions and corresponding regression curves of equivalent plastic strain against the projected contact diameter for various values of n at l/D=1% and 2r/d=0.4 for f=0.1. Equation (23) is the regression formula of $\epsilon_p$ expressed as a function of d and n. The curve from Eq. (23) for n=8.5 is also compared with the FE solution in FIG. 8. The good agreement indicates that Eq. (23) successfully characterizes $\epsilon_p$ as a function of d and n.

$$\varepsilon_p = f_o^\varepsilon(n)\left(\frac{d}{D}\right)^{f_1^\varepsilon(n)} \quad (23)$$

$$f_o^\varepsilon(n) = a_{oi}^\varepsilon n^{-i}; \ a_{oi}^\varepsilon = (1.82, -5.82, 6.92)$$

$$f_1^\varepsilon(n) = a_{1i}^\varepsilon n^{-i}; \ a_{1i}^\varepsilon = (1.45, -0.641, -0.233)$$

Figure 9:
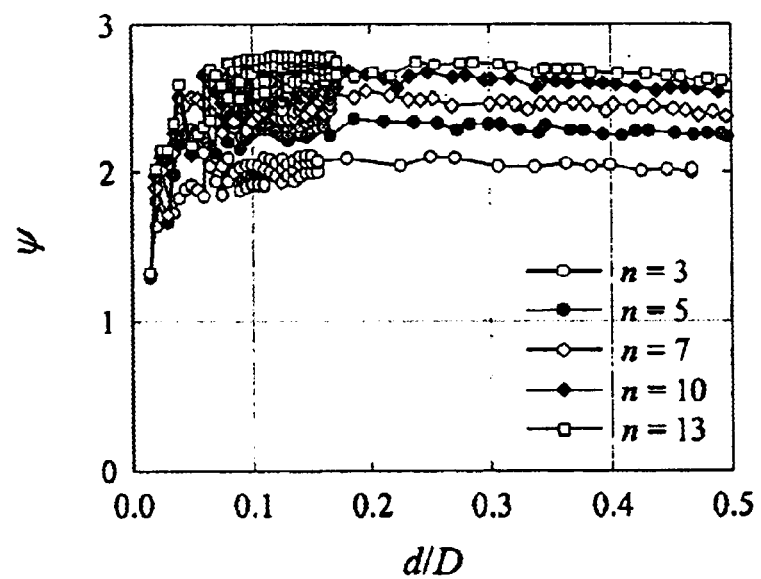
FIG. 9 is a graph for the constraint factor $\psi$ against projected contact diameter curve for various values of n.
Figure 10:
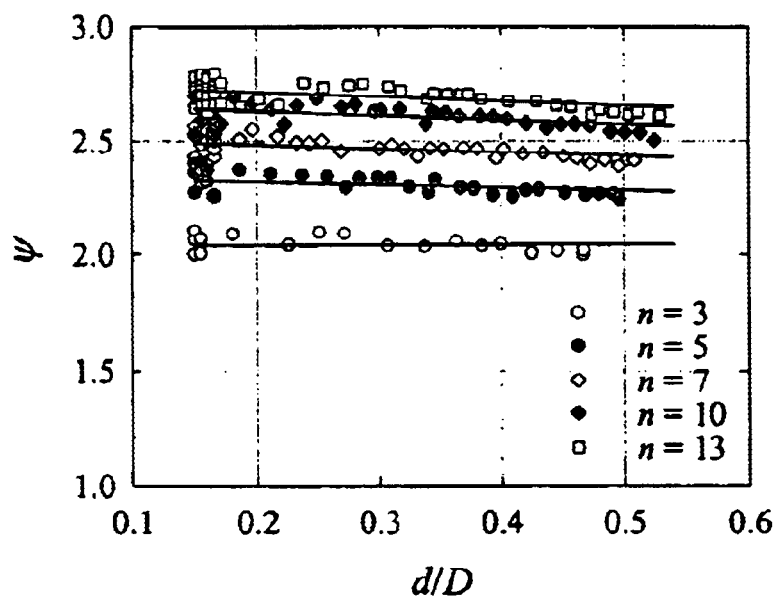
FIG. 10 is the generated curves with a constraint factor $\psi$ against the projected contact diameter as solid lines

FIG. 9 is the constraint factor $\psi$ against projected contact diameter curve for various values of n. At the outset of indentation, $\psi$ increases nonlinearly with d/D. Then, as plastic deformation becomes dominant after substantial indentation, it shows a linear relation with d/D (FIG. 10). Furthermore $\psi$ increases with n, which is consistent with the results of Matthews and Tirupataiah. But more importantly, even in sufficiently indented fully plastic state, $\psi$ keeps slightly decreasing, instead of saturating to a constant value, with indentation depth. In the range of d/D≧0/15, ψ can be given by the following linear expression.

$$\psi = f_o^\psi(n) + f_1^\psi(n)\left(\frac{d}{D}\right), (d/D \geq 0.15) \quad (24)$$

$$f_o^\psi(n) = a_{oi}^\psi n^{-i}; a_{oi}^\psi = (3.06, -4.4, 4.19)$$

$$f_1^\psi(n) = a_{1i}^\psi n^{-i}; a_{1i}^\psi = (-0.227, 0.317, 1.25)$$

The generated curves with the above expression are presented in FIG. 10 as solid lines. Equivalent stress (at the new data acquisition point) can be obtained by substituting ψ of Eq. (24) into Eq. (6).

Figure 11:
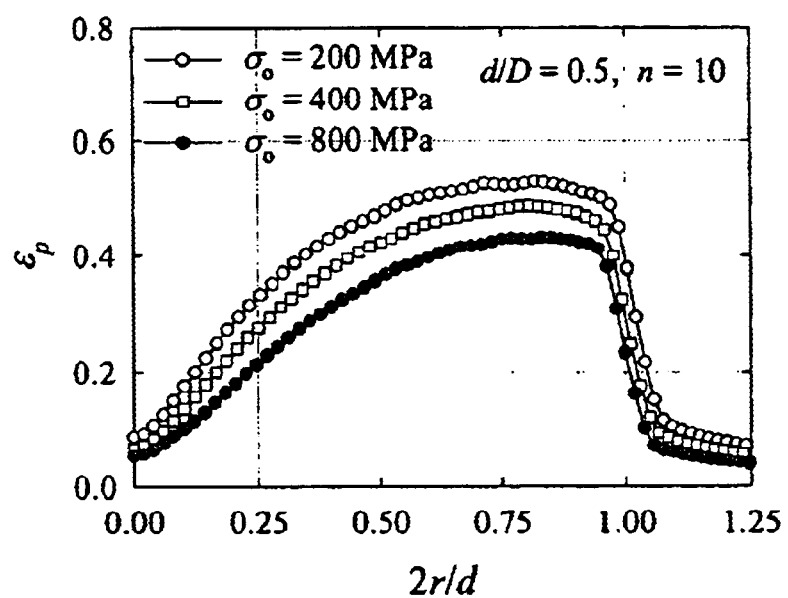
FIG. 11 is a distribution of equivalent plastic strain along the radial direction for three values of yield strength at d/D=0.5 with Young's modulus and fixed strain hardening exponent.

FIG. 11 shows the distribution of equivalent plastic strain along the radial direction for three values of yield strength ($\sigma_0$=200, 400, 800 MPa) at d/D=0.5 with Young's modulus (E=200 GPa) and strain hardening exponent (n=10) fixed. In such cases, the value of $\epsilon_p$ is observed to decrease with increasing yield strength for a given indentation depth. To clarify this kind of tendency, Young's modulus is additionally varied below.

Figure 12:
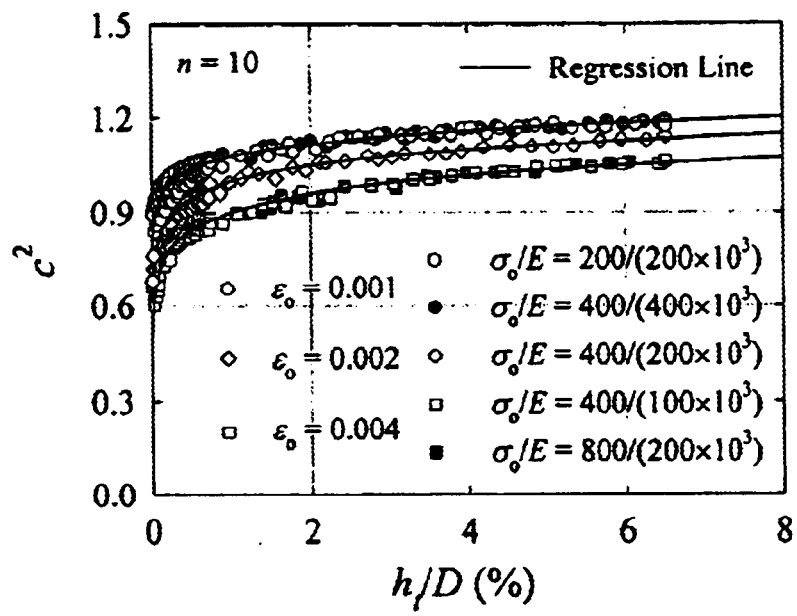
FIG. 12 is the relationships between $c^2$ and $h_r/D$ for various value of yield strain.

FIG. 12 shows the relationships between the $c^2$ and $h_r/D$ for various value of yield strain. It is noteworthy that identical yield strain produces the same curve regardless of absolute values of $\sigma_0$ and E; that is only the ratio $\sigma_0/E=\epsilon_0$ matters. The $c^2$ curve moves downward with increasing yield strain since the higher yield strain prolongs the initial dominance of elastic deformation. Yield strain determines the position of curve but barely affect the form of curve after transition region. For given n=10, each curves are almost parallel in fully plastic region.

Hence, it may be selected $\epsilon_0$ and n as two separate variables for governing the deformation characteristics of indentation in transition and fully plastic region, respectively. With separation of variable approach, $c^2$ of Eq. (22) becomes an integrated function of $\epsilon_0$ go and n as given in Eq. (25). The solid lines in FIG. 12 generated with the regression (25) agree well with the FE solutions represented by symbols.

$$c^2 = f_0{}^c(n)f_2{}^c(\epsilon_0) + f_1{}^c(n)f_3{}^c(\epsilon_0)\ln(100 h_r/D) \quad (25)$$

$$f_0{}^c(n) = a_{0i}{}^c n^{-1}; a_{0i}{}^c = (1.09, -1.21, 1.13)$$

$$f_1{}^c(n) = a_{1i}{}^c n^{-1}; a_{1i}{}^c = (0.104, -0.323, 0.405)$$

$$f_2{}^c(n) = a_{2i}{}^c \epsilon_0{}^1; a_{2i}{}^c = (1.19, -117, 11500)$$

$$f_3{}^c(n) = a_{3i}{}^c \epsilon_0{}^1; a_{3i}{}^c = (0.508, 345, -49500)$$

Figure 13:
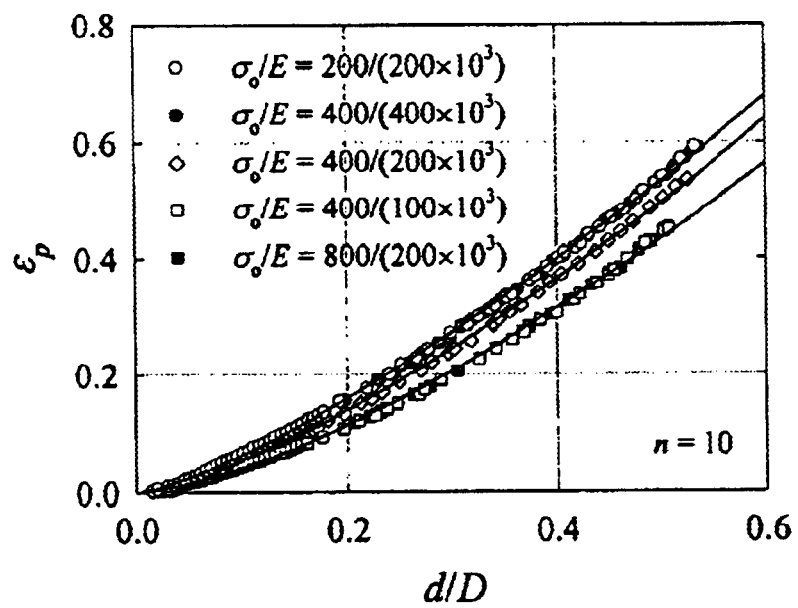
FIG. 13 is the effect of yield strain on $\epsilon_0$ vs. d/D curves.

FIG. 13 shows the effect of yield strain on $\epsilon_0$ vs. d/D curves. Equivalent plastic strain also decreases with higher yield strain for given d/D, since the higher yield strain prolongs the initial dominance of elastic deformation and delays plastic deformation. Equation (26) is an integrated regression formula extending Eq. (23) to various values of yield strain.

$$\epsilon_p = f_o^\epsilon(n) f_2^\epsilon(\epsilon_o)\left(\frac{d}{D}\right)^{f_1^\epsilon(n) f_3^\epsilon(\epsilon_o)} \quad (26)$$

$$f_o^\epsilon(n) = a_{oi}^\epsilon n^{-i}; a_{oi}^\epsilon = (1.82, -5.82, 6.92)$$

-continued $$f_1^\epsilon(n) = a_{1i}^\epsilon n^{-i}; a_{1i}^\epsilon = (1.45, -0.641, -0.233)$$

$$f_2^\epsilon(n) = a_{2i}^\epsilon \epsilon_o^j; a_{2i}^\epsilon = (1.05, -19.2, -3850)$$

$$f_3^\epsilon(n) = a_{3i}^\epsilon \epsilon_o^j; a_{3i}^\epsilon = (0.895, 66.7, -7090)$$

Figure 14A:
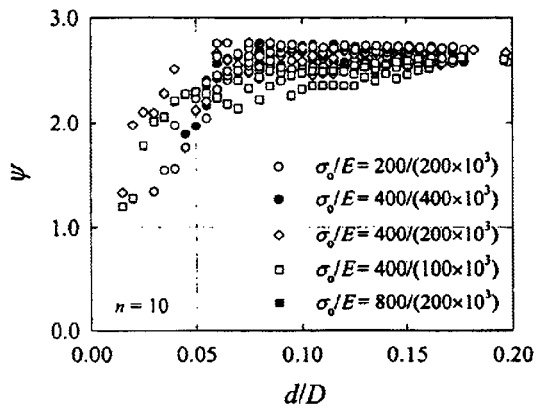
FIGS. 14(a) and 14(b) are the effect of yield strain on constraint factor $\psi$ vs. d/D curves, for the transition and fully plastic region, respectively.
Figure 14B:
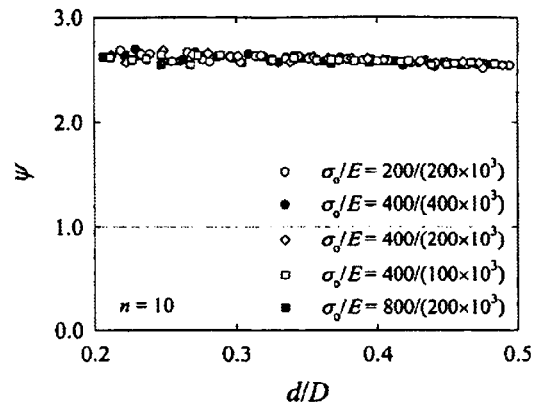

FIG. 14 shows the effect of yield strain on constraint factor ψ vs. d/D curves. FIG. 14(a) and FIG. 14(b) refer to transition and fully plastic region, respectively. While yield strain strongly affects ψ vs. d/D curve in transition region, it hardly affects the curve in fully plastic region. For the range of d/D≧0/15, ψ can be given by extending Eq. (24) to varying yield strain as:

$$\psi = f_o^\psi(n) f_2^\psi(\epsilon_o) + f_1^\psi(n) f_3^\psi(\epsilon_o)\left(\frac{d}{D}\right), (d/D \geq 0.15) \quad (27)$$

$$f_o^\psi(n) = a_{oi}^\psi n^{-i}; a_{oi}^\psi = (3.06, -4.4, 4.19)$$

$$f_1^\psi(n) = a_{1i}^\psi n^{-i}; a_{1i}^\psi = (-0.227, 0.317, 1.25)$$

$$f_2^\psi(n) = a_{2i}^\psi \epsilon_o^j; a_{2i}^\psi = (1.06, -30.3, 307)$$

$$f_3^\psi(n) = a_{3i}^\psi \epsilon_o^j; a_{3i}^\psi = (3.34, -1290, 61000)$$

Young's modulus in indentation test is primarily determined by the slope of unloading load-depth curve or by the amount of elastic recovery. Pharr et al. presumed that unloading load-depth curve is nonlinear, and the initial unloading slope of curve has a close relation with Young's modulus. Here a determining criterion is set up for initial unloading slope.

Figure 15:
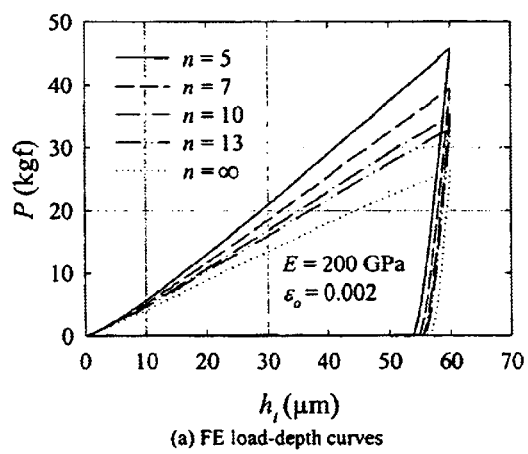
FIG. 15(a) is the load-depth curves obtained by FEA for a variety of material hardening exponent n with given Young's modulus and yield strain.
FIG. 15(b) is corresponding unloading slopes, S, abscissa r=P/$P_{max}$ measuring the portion of unloading curve used for linear regression.
Figure 15:
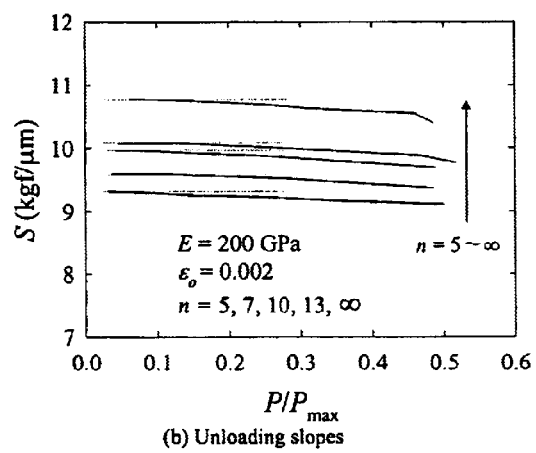

FIG. 15(a) shows load-depth curves obtained by FEA for a variety of material hardening exponent n with given Young's modulus and yield strain. FIG. 15(b) shows corresponding unloading slopes, S. Here abscissa r=P/$P_{max}$ measures the portion of unloading curve used for linear regression. That is, the portion $P_{max}$ to P is used for linear regression. The slope decreases with increasing regression range r, and it converges to a certain value for r<0.1. Thus this converged value may be defined as a initial unloading slope, and the slope should be measured for r=P/$P_{max}$<0.1.

Table 1 compares the slopes obtained from the regression range r=0.1 and r=0.5 for a variety of material properties. With the slopes for r=0.1 as references, the slopes for r=0.5 show errors of about 3%. The slope error increases with regression range r. Note again that the slope should be measured with r<0.1, since the slope error amplifies the total error of measured Young's modulus in addition to the inherent error of Young's modulus equations described below.

TABLE 1

| $\epsilon_o$ | E | n | S (r = 0.1) | S (r = 0.5) | Error (%) |
|---|---|---|---|---|---|
| 0.002 | 200 | 5 | 9.32 | 9.11 | 2.29 |
|  |  | 7 | 9.60 | 9.37 | 2.36 |
|  |  | 10 | 9.96 | 9.70 | 2.69 |
|  |  | 13 | 10.1 | 9.77 | 3.03 |
|  | 70 | 10 | 4.20 | 4.08 | 2.86 |
|  | 400 | 10 | 15.7 | 15.3 | 2.31 |

Pharr et al. presumed that unloading load-depth curve is essentially nonlinear, and the initial unloading slope, S, of load-depth curve has a close relation with Young's modulus.

They proposed following Young's modulus equation.

$$E = \frac{(1-\nu^2)}{d/S - (1-\nu_I^2)/E_I} \quad (28)$$

Here d is the actual projected indentation diameter with material pile-up/sink-in considered. Eq. (28) was originally derived under the assumption of a rigid cylindrical indenter penetrating the elastic plane specimen. That is, a plane indenter with circular cross-section indents into an elastic flat specimen. The concept of effective modulus was then introduced to include the deformation of indenter. Effective modulus, in a strict sense, never justifies the deformable indenter. At the instant of unloading, due to preceding plastic deformation, specimen is not flat but concave with a negative radius of curvature. Thus a correction coefficient is introduced into Eq. (28) so that it has the modified form:

$$E = \frac{(1-\nu^2)}{d/k_1 S - (1-\nu_I^2)/E_I} \quad (29)$$

Here the correction coefficient $k_1$ takes the real situation; a spherical deforming indenter, and a non-flat elastic-plastic specimen. To study the implication of $k_1$, Eq. (29) is recast as:

$$k_1 = \frac{d}{s}\left\{\frac{1-\nu^2}{E} + \frac{1-\nu_I^2}{E_I}\right\} \quad (30)$$

Figure 16:
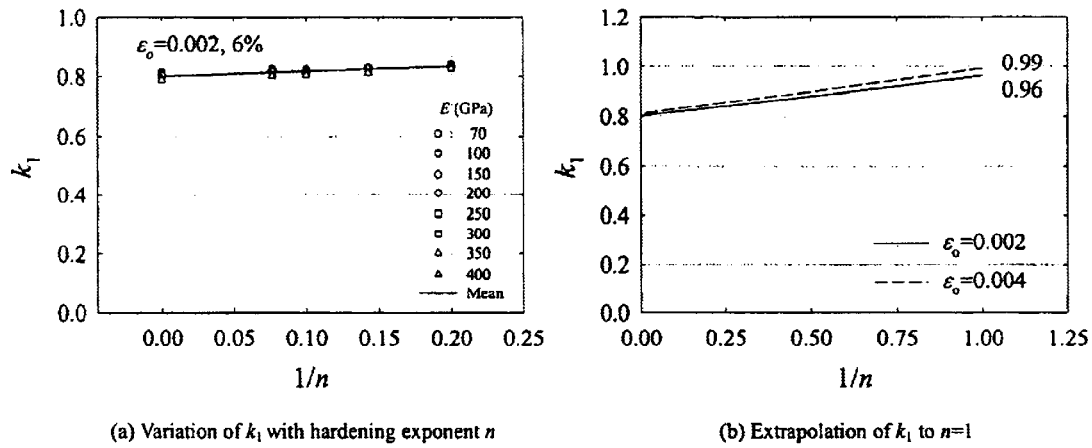
FIG. 16(a) is the variation of $k_1$ with respect to n for various values of E.
FIG. 16(b) is the extrapolation of $k_1$ with respect to n for various values of E.

FIG. 16(a) shows the variation of $k_1$ with respect to n for various values of E. It can be observed that $k_1$, slightly decreases with increasing n while $k_1$ is barely affected by E. For general metals having n values of 5~∞, it may be concluded $k_1$=0.83. FIG. 16(b) reveals that $k_1$ converges to 1 when n approaches to 1. In other words, for an elastic material, $k_1$ recovers Pharr's suggested value, 1.

Figure 17:
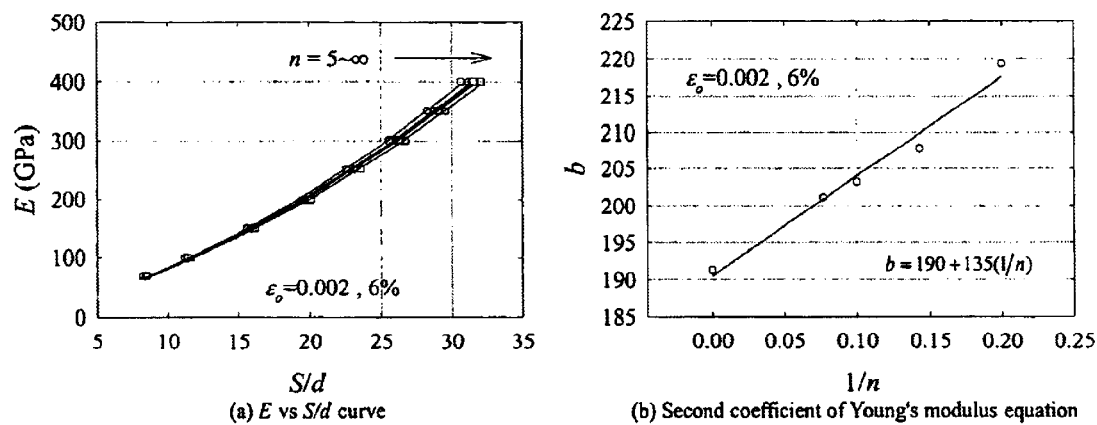
FIG. 17(a) is the FEA relationships between E and S/d for various values of n, when indentation depth is given as $h_r/D$=0.06.
FIG. 17(b) illustrates linear variation of b with 1/n, when a is fixed as 6200.

FIG. 17(a) shows FEA relationships between E and S/d for various values of n, when indentation depth is given as $h_r/D$=0.06. FIG. 17(a) suggests that E is an increasing function of S/d, and the coefficients of the function can be functions of n.

This observation leads us to:

$$E = a\left(\frac{S}{d}\right) + b\left(\frac{S}{d}\right)^2 \quad (31)$$

FIG. 17(b) shows linear variation of b with 1/n, when a is fixed as 6200. Incorporating this linear relation into (31) gives:

$$E = a\left(\frac{S}{d}\right) + b\left(\frac{S}{d}\right)^2 \quad (32)$$

$a$=6200, $b$=(173+8710$\epsilon_0$)+(93+21331$\epsilon_0$)(1/n)

Table 2 shows calculated values of Young's modulus from Eq. (5), and corresponding errors. Most of errors are within 2% and maximum error is 5%. Eq. 5 does not contain Young's modulus and Poisson's ratio of indenter. However it is never problematic considering fixed Young's modulus and Poisson's ratio of indenter in experiment.

TABLE 2

| E | n | $\epsilon_0$ = 0.002 | | | $\epsilon_0$ = 0.004 | | |
|---|---|---|---|---|---|---|---|
| | | S/d | E | Err (%) | S/d | E | Err (%) |
| 200 | 5 | 19.48 | 203 | 1.66 | 19.10 | 207 | 3.62 |
| | 7 | 19.59 | 202 | 1.01 | 19.20 | 205 | 2.50 |
| | 10 | 19.92 | 204 | 2.23 | 19.30 | 204 | 1.84 |
| | 13 | 19.78 | 201 | 0.64 | 19.58 | 206 | 3.16 |
| | ∞ | 20.09 | 201 | 0.74 | 20.00 | 207 | 3.61 |
| 70 | 10 | 8.40 | 67 | -5.00 | 8.31 | 67 | -4.07 |
| 100 | 10 | 11.43 | 97 | -2.53 | 11.33 | 99 | -0.78 |
| 150 | 10 | 15.95 | 151 | 0.57 | 15.59 | 152 | 1.03 |
| 250 | 10 | 23.16 | 253 | 1.21 | 22.68 | 257 | 2.69 |
| 300 | 10 | 26.16 | 302 | 0.67 | 25.50 | 310 | 3.30 |
| 350 | 10 | 28.98 | 351 | 0.31 | 28.34 | 357 | 1.97 |
| 400 | 10 | 31.46 | 397 | -0.74 | 30.38 | 397 | -0.82 |

Figure 18:
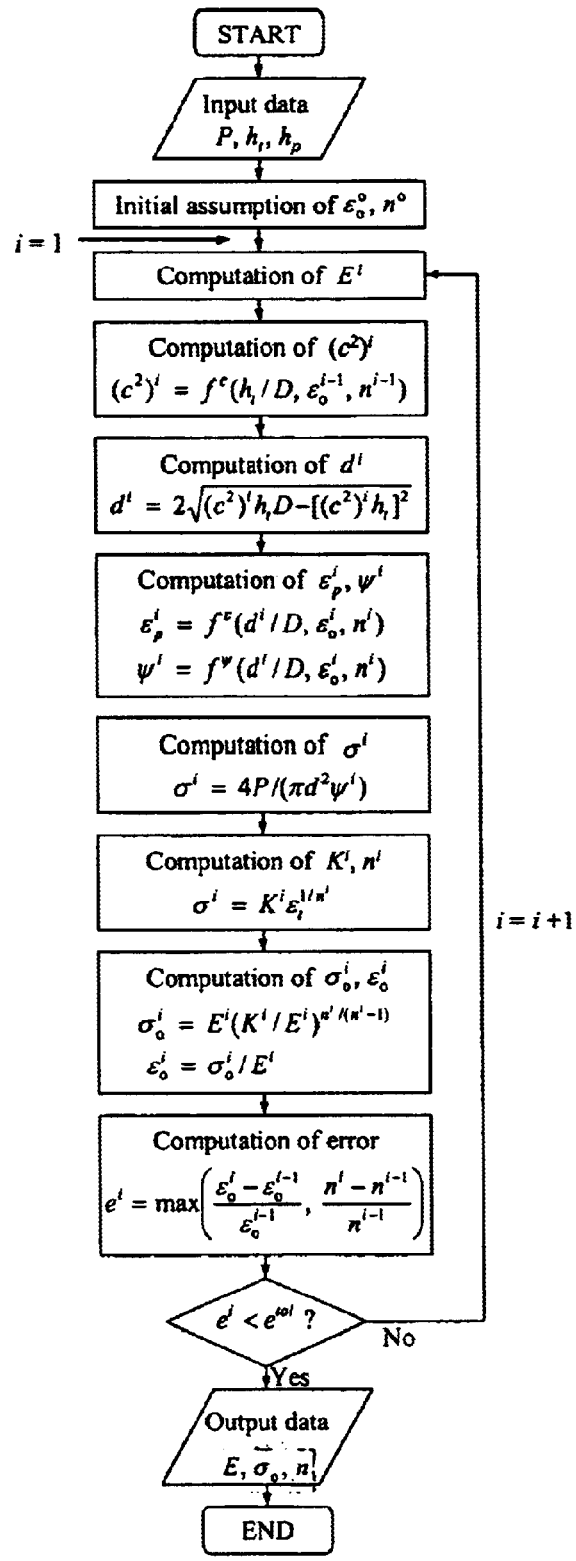
FIG. 18 is presently invented computing process of the material properties.

Synthesizing the above-mentioned argument, a program is prepared for evaluating material properties from indentation load-depth curve. The flow chart is shown in FIG. 18. Based on load-depth relation obtained from indentation test, material properties finally produced are Young's modulus, yield strength and strain hardening exponent.

In the approach of Haggag et al., each repetition of loading and unloading provides one of stress-strain data points. Thus a single indentation test usually picks up total only 6–7 data point, which results in a rather coarse regression. Haggag's theory requires prior material constants from extra tensile tests.

In the new approach, however, material properties are estimated using more than hundreds of data points obtained from a single time loading followed by unloading. New approach is also free from any extra test. It overall leads us to predict material properties in more accurate and simpler manners.

The load-depth curves are generated by using FE analyses for indentation depth of 6% of indenter diameter. Then, the load-depth curve is fed into the program to evaluate material properties. First, the Young's modulus E is computed from Eq. (29) by using slope S and initially guessed values of n and $\epsilon_0$. Then, $c^2$, $\epsilon_p$ and σ are calculated from Eqs. (25–27) as many as the number of load and depth data. From these, the values of n, K, $\sigma_0$ and $\epsilon_0$ are calculated from stress-strain relation. And then updated E, d, $c^2$, $\epsilon_p$, σ, n, K, $\sigma_0$ and $\epsilon_0$ are repeatedly calculated until the updated $\epsilon_0$ and n are converged within the tolerance.

Table 3 compares the predicted with real material properties. The average errors are less than 2% for E and $\sigma_0$, and 3% for n.

TABLE 3

| $\sigma_0$/E (×10$^{-3}$) | n | Computed $\sigma_0$/E (×10$^{-3}$) | Error (%) | Computed n | Error (%) |
|---|---|---|---|---|---|
| 400/200 | 5 | 429/198 | 7.3/1.0 | 5.44 | 8.8 |
| | 7 | 414/195 | 3.4/2.6 | 7.47 | 6.7 |
| | 10 | 404/202 | 1.1/0.8 | 10.4 | 4.0 |
| | 13 | 400/200 | 0.1/0.1 | 13.1 | 0.8 |
| 200/200 | 10 | 192/213 | 4.3/6.6 | 9.40 | 6.0 |
| 400/400 | | 387/422 | 3.2/5.5 | 9.63 | 3.7 |
| 400/100 | | 402/100 | 0.5/0.3 | 10.2 | 2.0 |
| 800/200 | | 798/202 | 0.3/0.8 | 9.92 | 0.8 |

Figure 19:
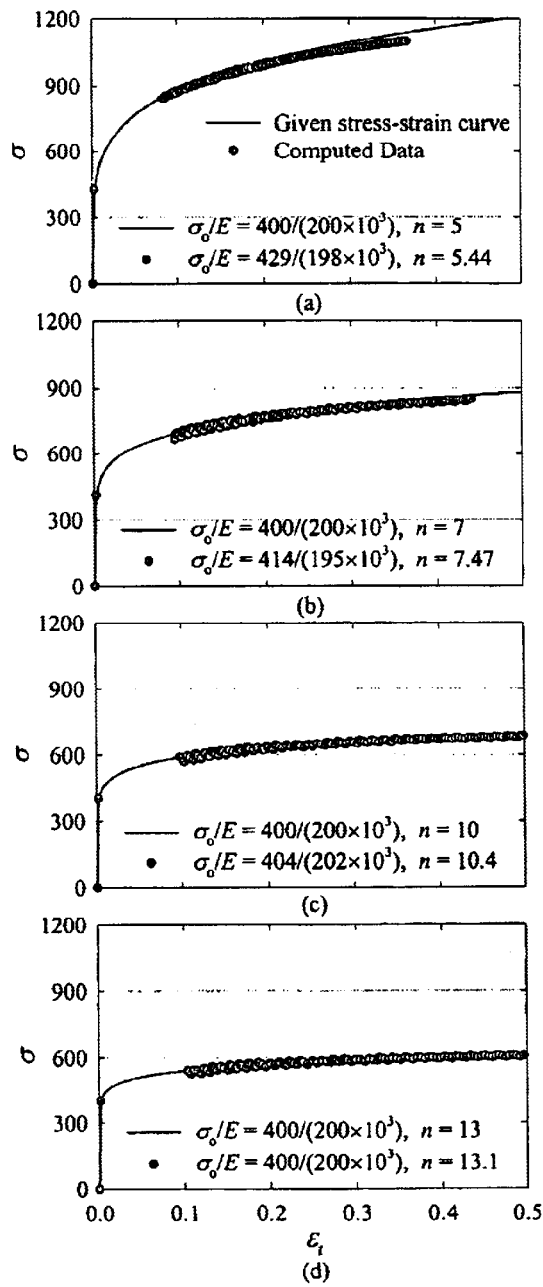
FIGS. 19 and 20 are the strain-stress curves via computing process of the present invention
Figure 20:
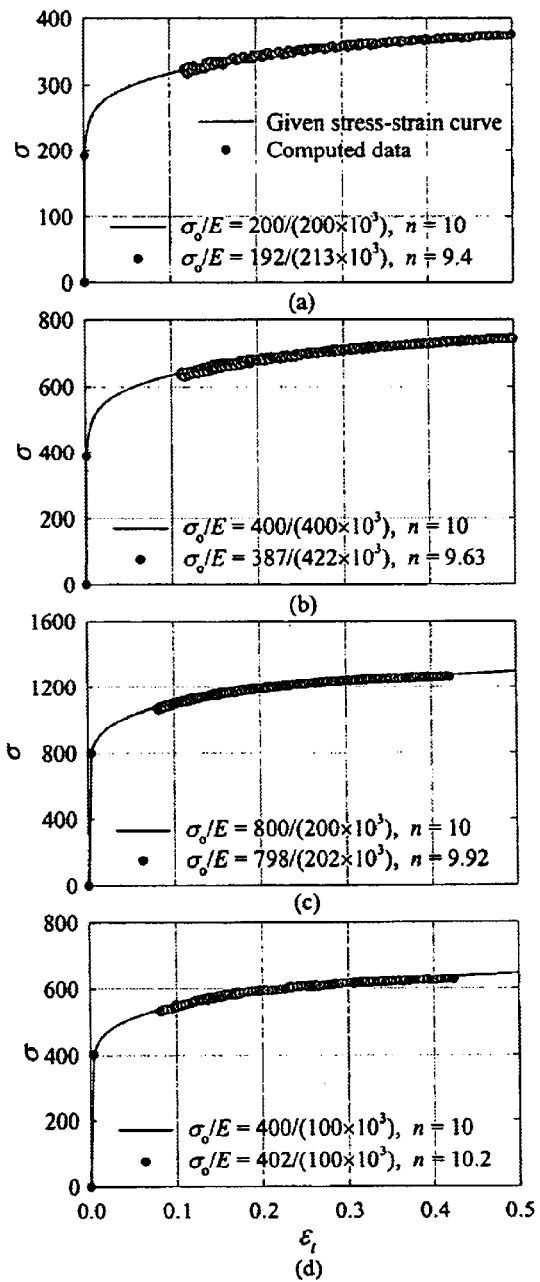

FIGS. 19 and 20 compare predicted and real material curves. Solid line is the material curve used for FEA, and symbol is the predicted stress-strain curve. These comparisons for various values of n and $\epsilon_0$ as shown in the figures more than validate our new approach.

The new theory increases the strain range by a factor of five. Enhancement of related functional equations (25) through (27) and (32), which substantially affect the accuracy of prediction, is in progress.

A new set of indentation governing equations is proposed based on the FE solutions. The load-depth curve from indentation test successfully converts to a stress-strain curve. The following remarks can be drawn from the above investigations.

(1) A new data acquisition point at 0.4 d apart from indentation center is selected. This new point features: i) negligible effect of friction coefficient, ii) quite gentle strain gradient and iii) extended strain range by a factor of five.

(2) The indentation variables $c^2$, $\epsilon_p$ and $\psi$ were regressed for various material properties from FE solutions of indentation analyses. From these, it reveals that the dominant parameters in indentation test are strain hardening exponent n and yield strain $\epsilon_0$.

(3) The previous indentation theories assuming constant $c^2$ without regard to indentation depth cannot be applied even for shallow indentation. The pile-up and sink-in parameter $c^2$ is generally a function of indentation depth as well as strain hardening exponent n.

(4) A new program is developed to evaluate material properties by using regression formulae of indentation variables $c^2$, $\epsilon_p$ and $\psi$. The load-depth curve is generated by FE analyses for indentation depth of 6% of indenter diameter once for all. The load-depth curves were converted to stress-strain curves, which provided material properties. The average errors of evaluated material properties were 2% for E and $\sigma_0$, and 3% for n.

(5) The previous theory based on experimental observation and deformation plasticity theory needs prior material constants from extra tensile tests. Moreover, the previous theory derives stress-strain relation with repetitive loading and unloading. However, our new approach based on flow theory can predict accurate material properties with a single loading followed by unloading without prior material constants.

Figure 21:
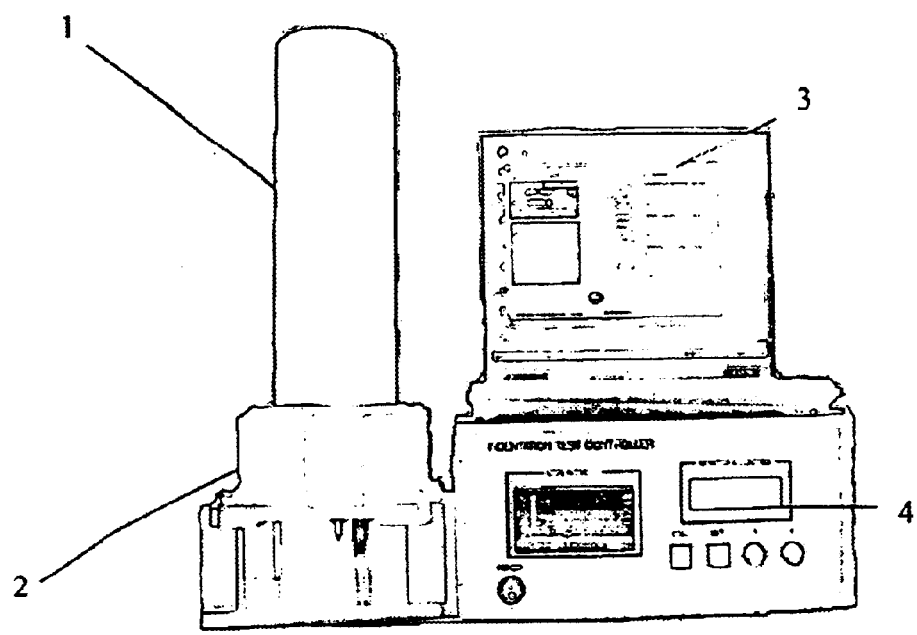
FIG. 21 is an automated indentation system with a stepmotor control system, measurement instrumentation, data acquisition system and control box of the present invention.

Based on the theories as discussed above, a non-destructive compression test utilizing the finite element solutions enables us to perform by the automated indentation system of the present invention The automated indentation system is comprised of the three parts: a stepmotor control system (1), measurement instrumentation (2), and data acquisition system (3) as shown in FIG. 21.

Figure 22:
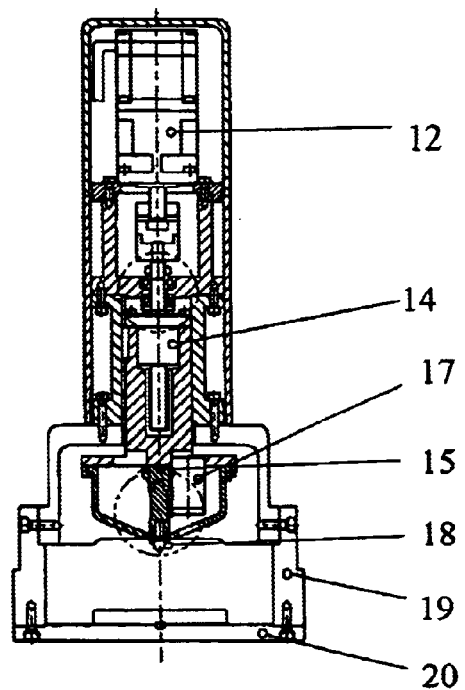
FIG. 22 is a front view of automated indentation system of an embodiment of the present invention.

FIG. 22 illustrates a schematic drawing of automated indentation system. Stepmotor (12) is suitable for applying to a micom of the present invention due to the pulse digital control, high static torque and smooth controlling of revolution speed. Therefore, a stepmotor (AS66AC-H50) is used in this system. The stepmotor controller enables to control the acceleration/deceleration and regulate the velocity with repeatability of 3~5%. A cylindrical linear actuator consists of a ball screw (14) (BTK 1404C, THK) and backlash nut (16) to suppress backlash. A flexible coupling (13) (SOH32C) connects the ball screw (14) and stepmotor for constraining the rotation and high repeatability.

The measurement instrumentation is comprised of a load cell (15), laser displacement sensor (17) for measuring the indentation depth, and ball indenter (18).

The load cells (15) with 200 kgf and 20 kgf of the maximum load are used and interchangeable. The load cell with 20 kgf is used for measuring material property of rubber.

The laser displacement sensor (model Z4M-N30V, OMRON) is used for measuring the indentation depth. The maximum movement (traveling distance) of laser displacement sensor (17) is 4 mm and resolution is 0.5 $\mu$m. The laser displacement sensor (17) is connected parallel to the linear actuator. The connecting socket lessens the additional compliance of system.

Figure 23:
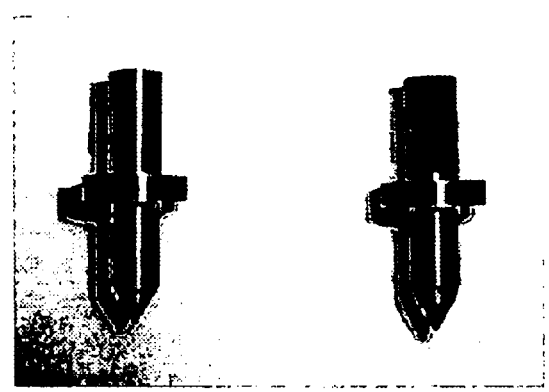
FIG. 23 illustrates integrated ball indenters

For a ball indenter (18) as shown in FIG. 23, an integrated spherical indenter made of tungsten carbide (WC) is used for precisely measuring the indented depth.

The Data Acquisition System (3) and Control Box (4) are shown in FIG. 21. The signals from the load cell (15) and laser displacement sensor (17) are amplified and filtered by signal amplifier. The amplified signal is graphed and stored in a file through PC program. The Data acquisition system (3) and motor controller (1) consist of a notebook PC and a control box (4) integrated for portability of indentation system.

Figure 24:
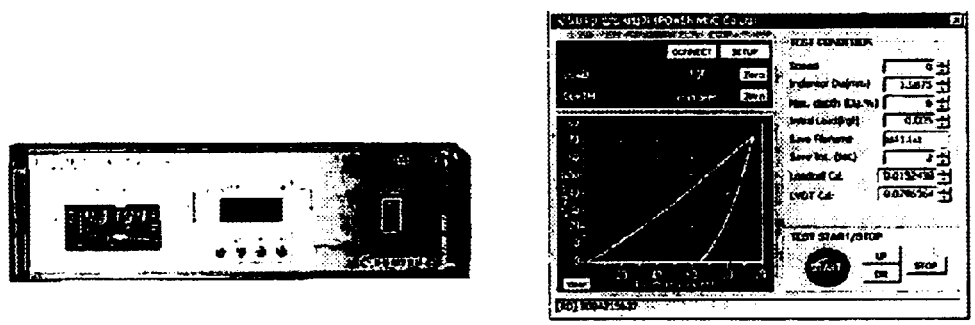
FIG. 24 illustrates a controlling box and a display of measured load-depth curve

The stepmotor (12) can be controlled with PC program as shown in FIG. 24. The moving speed and direction of the stepmotor (12) are also able to be adjusted by the control box (4). The control box (4) and program displayed on a window in PC enable to control the stepmotor (12) and perform the graphing and storing data of load-depth curve and material properties.

Figure 25:
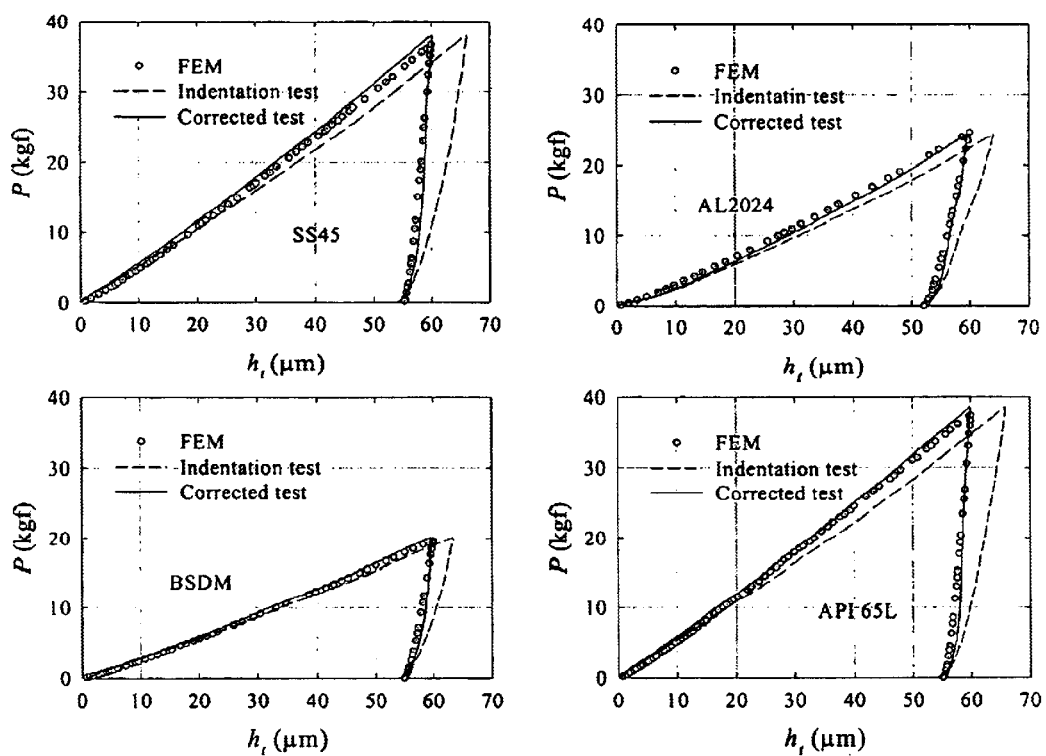
FIG. 25 illustrates the experimentally measured P-h curves after correcting $h_{add}$.

Dimensions of indentation system are H489×W220×D220 mm. The diameter of indenter tip is 1 mm. The indentation depth is measured by the laser displacement sensor which is non-contact optical instrument. For a given indentation depth, the indentation load is determined by indenter tip diameter and specimen material properties. If the obtained indentation depth from the FEA is a net displacement of indenter tip, the measured depth by the laser displacement sensor includes the compressed displacement between the indenter tip and the head part of the fixed laser displacement sensor. FIG. 25 shows P-h curves from the FEA and tests. The FEA adopted the material properties obtained from tensile test of the same material. The indentation load is controlled so that the maximum load of FEA and experiment are identical. Experimentally measured displacement contains additional displacement. Let $h_{exp}$ be the experimental indentation depth, and $h_{FEM}$ be the (actual) depth measured from FEA. Then, the additional displacement due to system compliance $h_{add}$ is $h_{exp}-h_{FEM}$. FIG. 25 shows experimentally measured P-h curves after correcting $h_{add}$. Consequently, the result is as same as that of the FEA solutions.

While the present invention has been described in detail with its preferred embodiments, it will be understood that its further modifications are possible. The present application is therefore intended to cover any variations, uses or adaptations of the invention following the general principles thereof, and includes such departures from the present disclosure as come within known or customary practice in the art to which this invention pertains within the limits of the appended claims.

What is claimed is:

1. An automated indentation system for performing a compression test by loading a compressive indentation load (P), thereby calculating an elastic modulus (E), yield strength ($\sigma_0$) and a hardening exponent (n) from measured indentation depth ($h_t$), indentation load (P) and unloading slope (S), comprises:

a step-motor control system (1) having a cylindrical linear actuator with a ball screw (14) and backlash nut (16) for suppressing backlash, a flexible coupling (13) being connected to said ball screw (14) and a step-motor (12) for constraining rotation and high repeatability, a measurement instrumentation (2) having a load cell (15), laser displacement sensor (17) for measuring the indentation depth, and an integrated ball indenter (18), a data acquisition system (3) having an signal amplifier for amplifying and filtering signals received from said load cell (15) and laser displacement sensor (17), and a control box (4) being pre-stored computer programming algorisms for adjusting and controlling moving speed and direction of said step-motor (12), performing calculations and plotting graphs of load-depth curves, strain-stress curves based on said amplified signal data, and said control box (4) for storing and retrieving measured signal data, material properties and produced data.

2. An automated indentation system as claimed in claim 1, wherein said step-motor control system (1) enables to control acceleration/deceleration of said step-motor (12) and regulating velocity with repeatability of 3~5%.

3. An automated indentation system as claimed in claim 1, wherein said load cell (15) is specified based on the performance of finite element simulation of indentation test, said load cells (15) with 200 kgf and 20 kgf of the maximum load are used and interchangeable.

4. An automated indentation system as claimed in claim 1, wherein said laser displacement sensor for measuring indentation depth is connected parallel to a linear actuator, and maximum traveling distance of said laser displacement sensor (17) is 4 mm and resolution is 0.5 μm.

5. An automated indentation system as claimed in claim 1, wherein said ball indenter (18) is an integrated spherical indenter being made of tungsten carbide (WC) for precisely measuring an indented depth, and a diameter of indenter tip is 1 mm.

6. An automated indentation system as claimed in claim 1, wherein a measured indentation depth ($h_{exp}$) being contained an additional displacement due to system compliance ($h_{add}$) is compensated by a displacement relationship between said measured indentation depth ($h_{exp}$) and an actual indentation depth ($h_{FEM}$) obtained from FEA.

7. An automated indentation system as claimed in claim 1, further comprises a computer programming algorism for calculating the elastic modulus (E), yield strength ($\sigma_0$) and hardening exponent (n) of the material during a performance of the non-destructive indentation test.

8. An automated indentation system as claimed in claim 7, further comprises a means for inputting data of measured indentation depth ($h_t$), load (P) and unloading slope (S) of the material from pre-stored data.

9. An automated indentation system as claimed in claim 7, further comprises a means for computing a contact diameter of the material between a ball tip and material surface.

10. An automated indentation system as claimed in claim 7, further comprises a means for computing a Young's modulus (E) from unload slope and initially guessed values of n and $\epsilon_0$ of the material.

11. An automated indentation system as claimed in claim 7, further comprises a means for computing indentation diameters (d) of the material from $c^2$ equation as many as the number of load and depth data, wherein the $C^2$ equation is defined as a ratio of actual indentation depth (h) to nominal depth ($h_t$) measured from the reference surface.

12. An automated indentation system as claimed in claim 7, further comprises a means for computing equivalent plastic strains ($\epsilon_p$) and equivalent stresses ($\sigma$) of the material according to the calculated indentation diameters (d).

13. An automated indentation system as claimed in claim 7, further comprises a means for computing values of strain hardening exponent (n) and K of the material from stress-strain relation.

14. An automated indentation system as claimed in claim 7, further comprises a means for computing a yield stress ($\sigma_0$) and strain ($\epsilon_0$) of the material.

15. An automated indentation system as claimed in claim 7, further comprises a means for computing updated E, d, $c^2$, $\epsilon_p$, $\sigma$, n, K, $\sigma_0$ and $\epsilon_0$ of the material until the updated $\epsilon_0$ and n are converged within the tolerance.

16. An automated indentation system as claimed in claim 7, further comprises a means for outputting material properties (E, $\sigma_0$, n) and plotting the stress-strain curve of the material.

* * * * *